United States Patent
Wood et al.

(10) Patent No.: US 7,000,613 B2
(45) Date of Patent: *Feb. 21, 2006

(54) NASAL INTERFACE AND SYSTEM INCLUDING VENTILATION INSERT

(75) Inventors: Thomas J. Wood, Blackshear, GA (US); Shara Hernandez, Miami, FL (US); Bruce M. Sher, Lighthouse Point, FL (US)

(73) Assignee: InnoMed Technologies, Inc., Coconut Creek, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/876,480

(22) Filed: Jun. 28, 2004

(65) Prior Publication Data

US 2005/0045182 A1 Mar. 3, 2005

Related U.S. Application Data

(63) Continuation-in-part of application No. 10/658,769, filed on Sep. 10, 2003.

(51) Int. Cl.
*A61M 16/00* (2006.01)
*A61M 15/08* (2006.01)

(52) U.S. Cl. .............................. 128/206.11; 128/207.18

(58) Field of Classification Search ........... 128/200.24, 128/202.18, 203.22, 203.29, 204.12, 205.25, 128/206.11, 206.12, 206.18, 206.21, 206.27, 128/206.28, 207.11, 207.14, 207.18, 207.15; 600/529, 532, 538
See application file for complete search history.

(56) References Cited

U.S. PATENT DOCUMENTS

| 1,125,542 | A | | 1/1915 | Humphries | |
|---|---|---|---|---|---|
| 1,818,028 | A | * | 8/1931 | Allen | 128/203.22 |
| 3,670,726 | A | | 6/1972 | Mahon et al. | |
| 3,739,774 | A | | 6/1973 | Gregory | |
| 3,861,385 | A | | 1/1975 | Carden | |
| 3,902,486 | A | | 9/1975 | Guichard | |
| 3,905,361 | A | | 9/1975 | Hewson et al. | |
| 4,156,426 | A | * | 5/1979 | Gold | 128/204.18 |
| 4,267,845 | A | | 5/1981 | Robertson, Jr. et al. | |
| 4,273,124 | A | | 6/1981 | Zimmerman | |
| 4,312,359 | A | | 1/1982 | Olson | |

(Continued)

FOREIGN PATENT DOCUMENTS

DE 146688 2/1981

(Continued)

OTHER PUBLICATIONS

SNAPP Nasal Interface, Tiara Medical Systems, Inc. http://www.tiaramed.com/asp_shop/shopdisplayproducts.asp?id=109&cat=SNAPP%2A+Nasal+Interface, viewed May 17, 2005.

*Primary Examiner*—Teena Mitchell
(74) *Attorney, Agent, or Firm*—Olds, Maier & Richardson, PLLC

(57) ABSTRACT

A ventilation or CPAP interface system adapted to be inserted into a nares of a user to secure the interface. A cannula adapted to be connected to a source of ventilation gas forms a first portion of an input gas flow passage to supply the ventilation gas to the user. A nasal insert adapted to be inserted the nares of the user forms a second portion of the input gas flow passage from the cannula to a distal end of the nasal insert. A seal portion adapted to engage a portion of the first naris is provided adjacent the distal end of the nasal insert. Ventilation interface system may optionally include feed tubes, y-connector, tube holder, headgear and a headgear flange.

25 Claims, 8 Drawing Sheets

U.S. PATENT DOCUMENTS

| | | | |
|---|---|---|---|
| 4,367,735 | A | 1/1983 | Dali |
| 4,367,816 | A | 1/1983 | Wilkes |
| 4,406,283 | A | 9/1983 | Bir |
| 4,422,456 | A | 12/1983 | Teip |
| 4,493,614 | A | 1/1985 | Chu et al. |
| 4,549,542 | A | 10/1985 | Chien |
| 4,587,967 | A | 5/1986 | Chu et al. |
| 4,601,465 | A | 7/1986 | Roy |
| 4,617,637 | A | 10/1986 | Chu et al. |
| 4,660,555 | A | 4/1987 | Payton |
| 4,699,139 | A | 10/1987 | Marshall et al. |
| 4,706,664 | A | 11/1987 | Snook et al. |
| 4,753,233 | A | 6/1988 | Grimes |
| 4,774,946 | A | 10/1988 | Ackerman et al. |
| 4,782,832 | A * | 11/1988 | Trimble et al. ........ 128/207.18 |
| 4,899,740 | A | 2/1990 | Napolitano |
| 4,915,105 | A | 4/1990 | Lee |
| 4,996,983 | A | 3/1991 | AmRhein |
| 5,000,173 | A | 3/1991 | Zalkin et al. |
| 5,022,900 | A | 6/1991 | Bar-Yona et al. |
| 5,025,805 | A | 6/1991 | Nutter |
| 5,038,772 | A | 8/1991 | Kolbe et al. |
| 5,046,491 | A | 9/1991 | Derrick |
| 5,074,297 | A | 12/1991 | Venegas |
| 5,113,857 | A | 5/1992 | Dickerman et al. |
| 5,121,745 | A | 6/1992 | Isreal |
| 5,127,397 | A | 7/1992 | Kohnke |
| 5,137,017 | A | 8/1992 | Salter |
| D333,015 | S | 2/1993 | Farmer et al. |
| 5,188,101 | A | 2/1993 | Tumolo |
| 5,265,592 | A | 11/1993 | Beaussant |
| 5,265,595 | A | 11/1993 | Rudolph |
| 5,269,296 | A | 12/1993 | Landis |
| 5,271,391 | A | 12/1993 | Graves |
| 5,299,599 | A | 4/1994 | Farmer et al. |
| 5,335,656 | A | 8/1994 | Bowe et al. |
| 5,355,893 | A | 10/1994 | Mick et al. |
| 5,372,130 | A | 12/1994 | Stern et al. |
| 5,375,593 | A | 12/1994 | Press |
| 5,385,141 | A | 1/1995 | Granatiero |
| 5,394,568 | A | 3/1995 | Brostrom et al. |
| 5,396,885 | A | 3/1995 | Nelson |
| 5,398,676 | A | 3/1995 | Press et al. |
| 5,400,776 | A | 3/1995 | Bartholomew |
| 5,425,359 | A | 6/1995 | Liou |
| 5,437,267 | A | 8/1995 | Weinstein et al. |
| 5,477,852 | A * | 12/1995 | Landis et al. .......... 128/207.18 |
| 5,509,409 | A | 4/1996 | Weatherholt |
| 5,526,806 | A | 6/1996 | Sansoni |
| 5,533,506 | A | 7/1996 | Wood |
| 5,682,881 | A | 11/1997 | Winthrop et al. |
| 5,740,799 | A | 4/1998 | Nielson |
| 5,794,619 | A | 8/1998 | Edelman et al. |
| 5,906,203 | A | 5/1999 | Klockseth et al. |
| 5,954,049 | A | 9/1999 | Foley et al. |
| 5,975,077 | A * | 11/1999 | Hofstetter et al. ..... 128/204.24 |
| 6,561,188 | B1 | 5/2003 | Ellis |
| 6,561,193 | B1 | 5/2003 | Noble |
| 6,571,798 | B1 | 6/2003 | Thornton |
| 6,595,215 | B1 | 7/2003 | Wood |
| 6,637,434 | B1 | 10/2003 | Noble |
| 6,655,385 | B1 | 12/2003 | Curti et al. |
| 6,679,265 | B1 * | 1/2004 | Strickland et al. ...... 128/207.18 |
| 6,766,800 | B1 | 7/2004 | Chu et al. |
| 2002/0046755 | A1 | 4/2002 | DeVoss |
| 2002/0124849 | A1 | 9/2002 | Billette de Villemeur |
| 2005/0028822 | A1 | 2/2005 | Sleeper et al. |
| 2005/0033247 | A1 | 2/2005 | Thompson |
| 2005/0051176 | A1 | 3/2005 | Riggins |
| 2005/0061326 | A1 | 3/2005 | Payne, Jr. |

FOREIGN PATENT DOCUMENTS

| | | |
|---|---|---|
| EP | 93309991.3 | 6/1995 |
| GB | 0532214 | 1/1941 |
| WO | WO 01/97892 A1 | 6/2000 |
| WO | WO 03/066145 | 8/2003 |
| WO | WO 03/066146 | 8/2003 |
| WO | WO 2005/079726 | 9/2005 |

* cited by examiner

SECTION I-I

SECTION II - II

SECTION III-III

NASAL INTERFACE AND SYSTEM INCLUDING VENTILATION INSERT

CROSS REFERENCE TO RELATED APPLICATIONS

This application is a Continuation-in-Part of co-pending application Ser. No. 10/658,769, filed on Sep. 10, 2003, the entire contents of which are hereby incorporated by reference and for which priority is claimed under 35 U.S.C. §120.

This application is related in subject matter to U.S. Pat. No. 6,478,026, PCT patent application No. PCT/US03/24590, filed Aug. 6, 2003, U.S. patent application Ser. No. 10/610,594 filed Jul. 2, 2003, Ser. No. 10/044,925 filed Jan. 15, 2002, Ser. No. 10/096,795 filed Mar. 14, 2002, and Ser. No. 10/392,959 filed Mar. 21, 2003, all to Thomas J. Wood, the disclosures of which are incorporated by reference herein in their entirety.

BACKGROUND OF THE INVENTION

1. Field of the Invention

Exemplary embodiments of the invention are directed to a ventilation interface, and more particularly to a ventilation interface including a cannula forming a first portion of an input gas flow passage and a nasal insert forming a second portion of the input gas flow passage, the first and second portions of the input gas flow passage disposed at an obtuse angle to one another.

2. Discussion of Related Art

Obstructive sleep apnea syndrome (commonly referred to as obstructive sleep apnea, sleep apnea syndrome, and/or sleep apnea) is a medical condition characterized by repeated, prolonged episodes of cessation of breathing during sleep. During a period of wakefulness, the muscles of the upper part of the throat passage of an individual keep the passage open, thereby permitting an adequate amount of oxygen to flow into the lungs. During sleep, the throat passage is narrowed due to the relaxation of the muscles. In those individuals having a relatively normally sized throat passage, the narrowed throat passage remains open enough to continue to permit the adequate amount of oxygen to flow into the lungs. However, in those individuals having a relatively smaller sized throat passage, the narrowed throat passage prohibits the adequate amount of oxygen from flowing into the lungs. Additionally, one or more of a nasal obstruction, a relatively large tongue, and/or certain shapes of the palate and/or the jaw of the individual further prohibit the adequate amount of oxygen from flowing into the lungs.

The individual having the above-discussed conditions can stop breathing for one or more prolonged periods of time (e.g., each period of time being 10 seconds or more). The prolonged periods of time during which breathing is stopped, or apneas, are generally followed by sudden reflexive attempts to breathe. The reflexive attempts to breathe are generally accompanied by a change from a relatively deeper stage of sleep to a relatively lighter stage of sleep. As a result, the individual suffering from obstructive sleep apnea syndrome generally experiences fragmented sleep that is not restful. The fragmented sleep results in one or more of excessive and/or inappropriate daytime drowsiness, headache, weight gain or loss, limited attention span, memory loss, poor judgment, personality changes, lethargy, inability to maintain concentration, and/or depression.

Other medical conditions can also prevent individuals, including adults and infants, from receiving the adequate amount of oxygen into the lungs. For example, an infant who is born prematurely can have lungs that are not developed to an extent necessary to receive the adequate amount of oxygen. Further, prior to, during, and/or subsequent to certain medical procedures and/or medical treatments, an individual can be unable to receive the adequate amount of oxygen.

Under these circumstances, it is known to use a ventilation interface to apply a positive pressure to the throat of the individual, thereby permitting the adequate amount of oxygen to flow into the lungs. In the known ventilation interface, oxygen and/or room air containing oxygen is delivered through the mouth and/or nose of the individual. Known types of positive pressure applied by the known ventilation interface include continuous positive airway pressure (CPAP) in which a positive pressure is maintained in the throat passage throughout a respiratory cycle, bilevel positive airway pressure (BiPAP) in which a relatively high positive pressure is maintained during inspiration and a relatively low positive pressure is maintained during expiration, and intermittent mechanical positive pressure ventilation (IPPV) in which a positive pressure is applied when apnea is sensed (i.e., the positive airway pressure is applied intermittently or non-continuously).

A known ventilation interface for the application of such positive pressures includes a conventional face mask that covers the nose and/or mouth, as well as a conventional pair of nasal pillows that are inserted into corresponding nares of the naris.

The conventional face mask requires a harness, such as a headband and/or other headgear components, to provide and maintain a required fluid or gas tight seal between the mask and the face of the individual. Additionally, the conventional tubing will collapse if it is bent around the ears with the flat side against the side of the users head. Thus, the use of such a conventional harness and tubing results in a number of disadvantages.

For example, because pressure must be applied between the required harness and the head of the individual to maintain the required seal, the harness is generally uncomfortable, particularly when sleeping. The applied pressure often results in undesirable irritation and sores caused by movement of the mask and harness during periods of both wakefulness and sleep. Further, the required seal is generally unable to be maintained when the mask and harness is moved. The mask also generally applies an undesirable pressure to the sinus area that is adjacent to the nose, causing the nasal sinus airways to narrow, thereby increasing a velocity of flow through the upper anatomical airways and decreasing lateral pressure against the nasal mucosal walls. Further, the tubing may fold undesirably further exacerbating the above problem. The above-discussed combination of increased flow velocity and decreased pressure results in the removal of moisture from the mucosal walls during inspiration, causing an undesirable drying and a burning sensation within the nares. As a result, the individual may remove the mask to alleviate these discomforts, consequently discontinuing the beneficial application of the positive pressure.

The conventional nasal pillows include pillowed style nasal seals that are pressed against the bottom portion of the nares. However, the known nasal pillows also require the use of a harness to keep the nasal pillows pressed against the bottom of the nares, resulting in disadvantages similar to those of the conventional face mask.

For these reasons, it is desirable to provide a nasal interface and system that overcomes one or more of the above-discussed disadvantages.

SUMMARY OF THE INVENTION

Exemplary embodiments of the present invention provide a ventilation interface adapted to be inserted into a nares of a user to secure the interface. A cannula adapted to be connected to a source of ventilation gas forms a first portion of an input gas flow passage to supply the ventilation gas to the user. A nasal insert adapted to be inserted into the nares of the user forms a second portion of the input gas flow passage from the cannula to a distal end of the nasal insert. A seal portion adapted to engage a portion of the first nares can be provided adjacent the distal end of the nasal insert. The first and second portions of the input gas flow passage are disposed at an obtuse angle to one another.

In another exemplary embodiment of the invention, a gas output forms a portion of an output gas flow passage from the nasal insert to an exterior of the ventilation interface to channel a gas expired by the user. Optionally, the second portion of the input gas flow passage and the portion of the output gas flow passage can be configured to provide laminar flow therebetween.

In yet another exemplary embodiment, the seal portion of the nasal insert forms a seal with the naris of the user by optionally a resiliency of the seal portion of the nasal insert or a resiliency of the nares of the user or some combination of the two. Further, at least one of the nasal insert and the seal portion may, optionally, be sufficiently flexible to be expanded by a positive pressure provided by the ventilation gas to help form a seal portion.

Exemplary embodiments of the present invention further provide a ventilation interface adapted to be inserted into a nares of a user which can secure the interface. A first subassembly forms a first portion of an input gas flow passage from a ventilation gas supply source. A second subassembly forms a second portion of the input gas flow passage from the first subassembly to a first naris of the nares of the user. A subassembly for engaging a portion of the first naris is provided on the second subassembly. The first and second portions of the input gas flow passage are disposed at an obtuse angle to one another.

Exemplary embodiments of the present invention further provide a feed tube and y-connector adapted for use in a ventilation interface system. The feed tube having an annular sleeve and may optionally include a first exterior portion and a second exterior portion; the first exterior portion including a plurality of first ribs and a second exterior portion including a plurality of second ribs.

Yet further exemplary embodiments of the present invention provide a ventilation interface system including a cannula adapted to be connected to a source of ventilation gas via a feed tube and a y-connector, the cannula forming a first portion of an input gas flow passage to supply the ventilation gas to the user. A nasal insert adapted to be inserted the nares of the user, the nasal insert forming a second portion of the input gas flow passage from the cannula to a distal end of the nasal insert. A seal portion adapted to engage at least a portion of the nares of the user, the seal portion provided adjacent the distal end of the nasal insert wherein the first and second portions of the input gas flow passage are disposed at an obtuse angle to one another. Optionally, head or harness gear may be provided to assist in holding the nasal inserts in place.

In another exemplary embodiment, the headgear's interaction with the headgear flange may hold the nasal inserts in the nares of a user. Further, a thin skirt may optionally be wrapped around the ridges of the nasal insert and may assist in preventing leaks.

BRIEF DESCRIPTION OF THE DRAWINGS

A more complete appreciation of the exemplary embodiments of the present invention, and one or more of the attendant advantages thereof, will be readily ascertained and/or obtained as the same becomes better understood by reference to the following detailed description when considered in connection with the accompanying drawings, wherein.

DETAILED DESCRIPTION OF THE EXEMPLARY EMBODIMENTS

Figure 1:
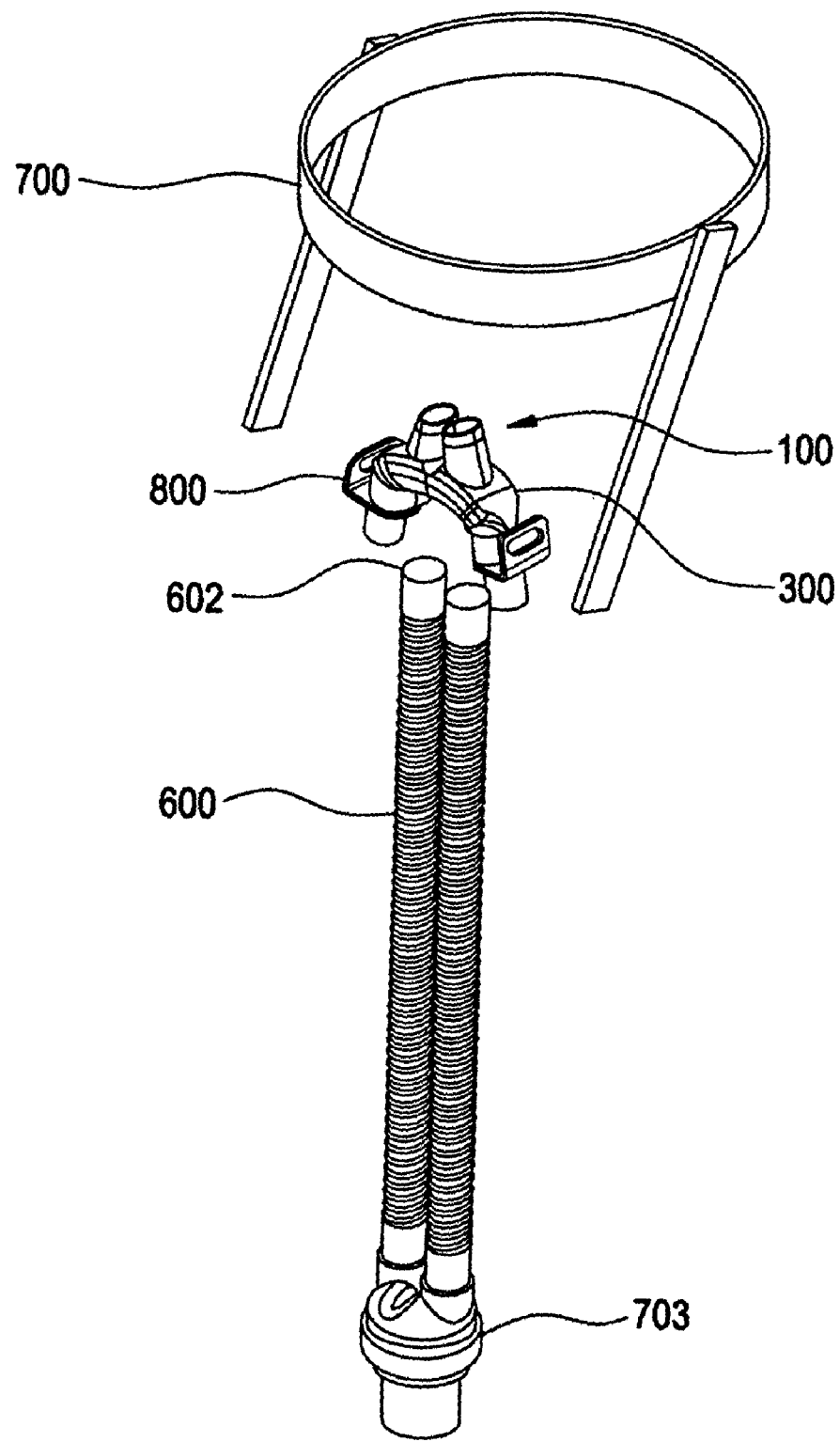
FIG. 1 shows an exploded side elevation view of a first exemplary embodiment of the ventilation interface system.
Figure 2:
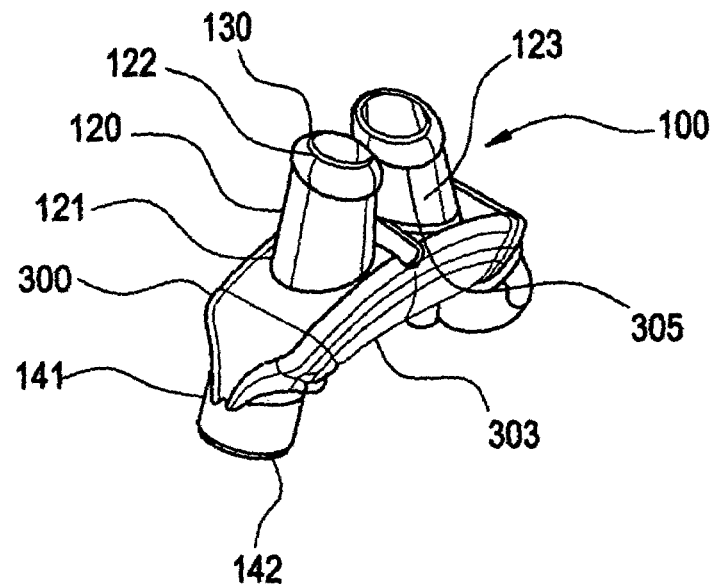
FIG. 2 shows a side elevation view of a ventilation insert.
Figure 3:
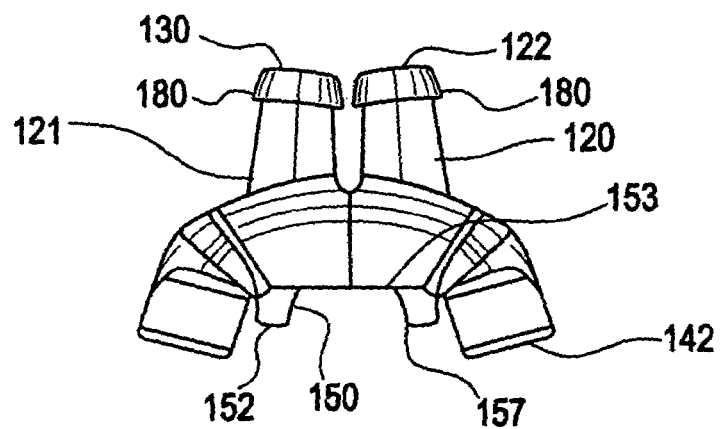
FIG. 3 shows a side view of the ventilation insert of FIG. 2.
Figure 4:
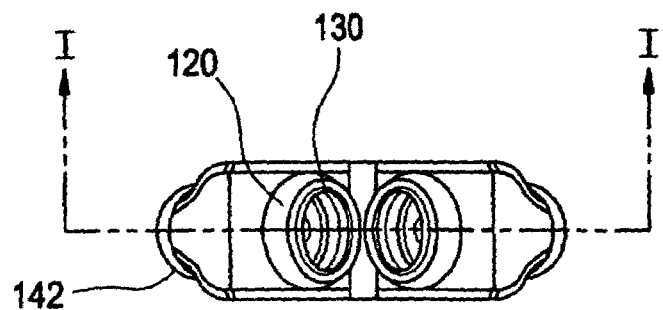
FIG. 4 shows a top view of the ventilation insert of FIG. 2.
Figure 5:
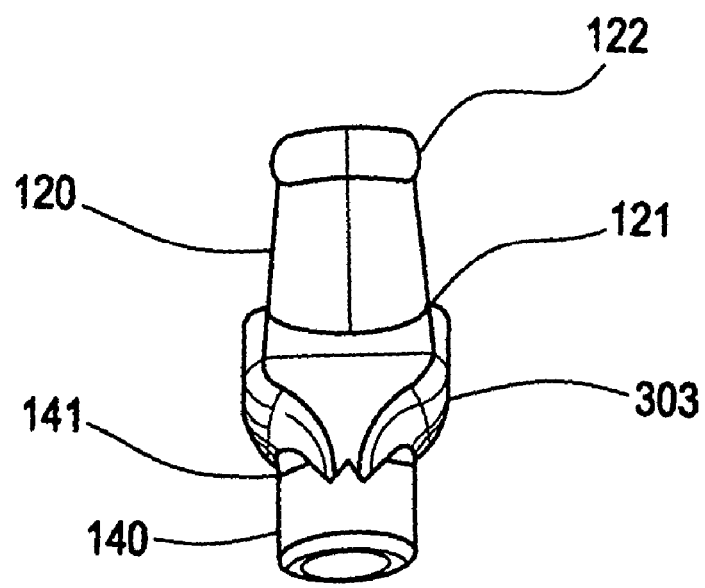
FIG. 5 shows a side view of the ventilation insert of FIG. 2.
Figure 6:
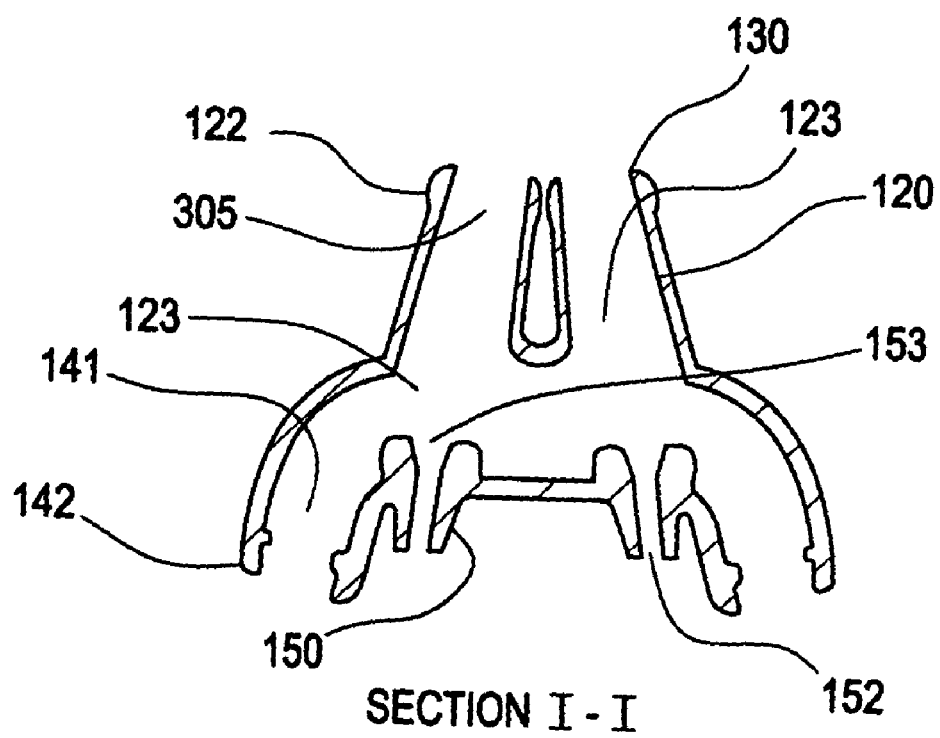
FIG. 6 shows a cross-sectional view taken from line I—I in FIG. 3.
Figure 7:
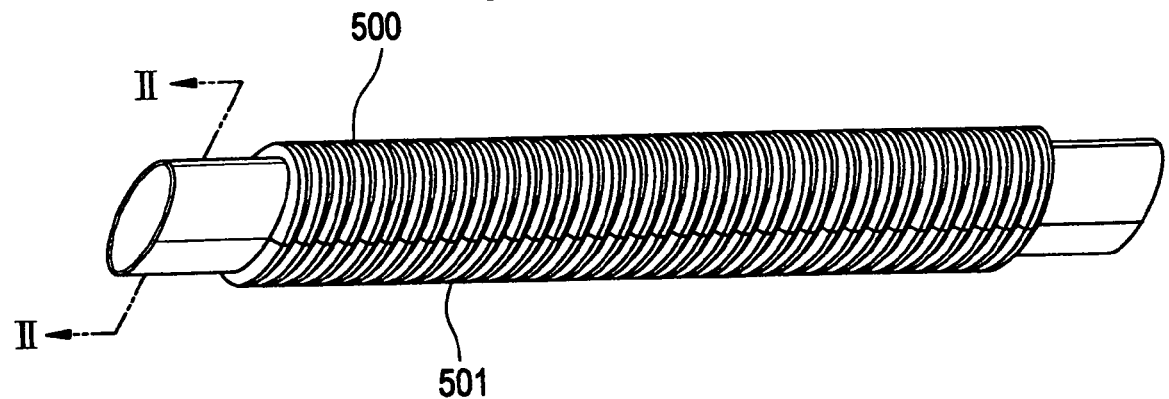
FIG. 7 shows an elevated side view of an oval feed tube.
Figure 8:
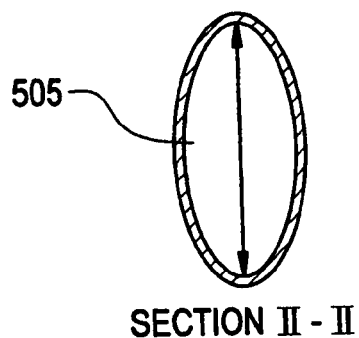
FIG. 8 shows a cross-sectional view of a feed tube taken along line II—II in FIG. 7.

Examples of one or more exemplary embodiments of the present invention will now be described with reference to the drawings, wherein like reference numbers throughout the several views identify like and/or similar elements.

Generally referring to FIGS. 1–20, exemplary embodiments of the present invention can provide a ventilation interface system adapted to be inserted into a nares of a user to secure the interface. A cannula 300 adaptable to be connected to a source of ventilation gas (not shown) forms a first portion 141 of an input gas flow passage to supply the ventilation gas to the user. Nasal inserts 120 are adapted to be inserted into the nares of the user forms a second portion 123 of the input gas flow passage from the cannula to a distal end of the nasal insert 130. A seal portion 122 optionally adapted to engage a portion of the nares of the user is positioned at the distal end 130 of the nasal insert. The first 141 and second portions 123 of the input gas flow passage may be disposed at an obtuse angle to one another.

In another exemplary embodiment of the invention, the obtuse angle is between about 110° and about 170°, and more preferably the obtuse angle is about 135°.

In a further exemplary embodiment of the invention, gas output flow passages 150, form a portion of an output gas flow passage from the nasal insert 120 to an exterior of the ventilation interface to channel a gas expired by the user. Optionally, the second portion 123 of the input gas flow passage formed by the nasal insert is about parallel with the portion of the output gas flow passage 150. Moreover, the second portion 123 of the input gas flow passage and the portion of the output gas flow passage 150 are configured to, optionally, provide laminar flow therebetween.

In yet another exemplary embodiment, the nasal inserts 120, and the seal portions 122 form a seal with the nares of the user by, optionally, a resiliency of the seal portion 122 and nasal insert 120 or a resiliency of the nares of the user or some combination of the above with a headgear 700 assisting in gently holding the nasal insert 120 into the nares. Alternatively, the headgear 700 may be configured to be attached to headgear flange 800, 801. Further, at least one of the nasal inserts 120 and the seal portions 122 may, optionally, be sufficiently flexible to be expanded by a positive pressure provided by the ventilation gas to help form a seal with the nares of the user. Additionally, a skirt 180 may be attached to the portion 122 of the nasal insert 120 to prevent leakage.

Specifically, as shown in the FIGS. 1–20 exemplary embodiments of a ventilation interface 100 of the present invention can include, among other components, a cannula 300, nasal inserts 120, seal portions 122 and gas outputs 150, to be described below.

The cannula 300 can be adapted to be connected to a source of ventilation gas (not shown), such as oxygen and/or room air containing oxygen, to apply a positive pressure to the throat of the user of the ventilation interface 100, thereby permitting an adequate amount of oxygen to flow into the lungs. Optionally, the system may be connected to a mechanical ventilator. Although the figures show certain exemplary embodiments of the cannula 300, it is to be understood that the cannula 300 can be of any type, so long as the cannula 300 can be connected to the source of the ventilation gas.

The cannula 300 can include a distal end 142 connectable to the source of the ventilation gas via a feed tube 500, 600. In an exemplary embodiment of the invention, the y-connector 703 can include an exterior surface and an interior surface defining a wall portion therebetween, each of the exterior and interior surfaces having optionally substantially circular or oval cross section. By this arrangement, the y-connector 703 can be connected with the source of the ventilation gas at one end and to the feed tube at the other end 500, 600.

The cannula 300 can include a cannula body 303 adjacent to distal end 142 that defines a first portion 141 of the input gas flow passage, and more specifically can define the second portion 123 of the input gas flow passage through the cannula body 303. The cannula body 303 can define a portion of an output gas flow passage, and, more specifically, can define the fourth portion 153 of the output gas flow passage from the nasal insert 120 through the cannula body 303 (discussed below). The cannula body 303 can extend along one or more axes such that laminar flow can be achieved within the second portion 123 of the input gas flow passage and/or such that laminar flow can be achieved within the fourth portion 153 of the output gas flow passage. Further, the cannula body 303 can extend along the one or more axes such that laminar flow can be achieved between the second portion 123 of the input gas flow passage and portions of the input gas flow passage upstream and/or downstream of the second portion, and/or can extend along the one or more axes such that laminar flow can be achieved between the fourth portions 153 and the second portions 123 of the output gas flow passage. Optionally, portions of the axes of the second portion 123 of the input gas flow passage and/or the fourth portion 153 of the output gas flow passage extend along a substantially arcuate line.

The nasal insert 120 can be disposed adjacent the cannula body 303 and can be adapted to be inserted the nares of the user to apply the positive pressure to the throat of the user. Although the figures show certain exemplary embodiments of the nasal insert 120, it is to be understood that the nasal insert 120 can be of any type, so long the nasal insert 120 can be inserted into the nares to apply the positive pressure.

The nasal insert 120 can define a third portion 305 and a fourth portion 153 of the input gas flow passage, and more specifically can define the third 305 and fourth 153 portions of the input gas flow passage from the cannula 300 through the nasal insert 120. The nasal insert 120 can define a second portion 123 and a third portion 305 of the output gas flow passage, and more specifically can define the second 123 and third 305 portions of the output gas flow passage from the sealing portion 122 through the nasal insert 120. In an exemplary embodiment of the invention, the nasal insert 120 can include an exterior surface and an interior surface defining a wall portion therebetween, each of the exterior and interior surfaces may have a varying cross section including oval shapes or, optionally, substantially circular or flat shapes, such that the nasal inserts 120 can define the above-identified flow passages.

The nasal insert 120 can have a maximum interior cross sectional area and circumference at a proximal end 121 of the nasal insert 120 that is adjacent the cannula 300, thereby defining the third portion 305 of the input/output gas flow passage. The nasal insert 120 may optionally have a minimal interior cross sectional area and circumference at a distal end 130 of the nasal insert 120 that is disposed away from the cannula 300 (i.e., opposite the proximal end 121), thereby defining the fourth portion 153 of the input/output gas flow passage, and thereby defining the second portion 123 of the input/output gas flow passage. Optionally, the nasal insert 120 may have the substantially same interior cross sectional area and circumference at the distal 130 and proximal ends 121. In an exemplary embodiment of the invention, the proximal end 121 may, optionally, be in the form of an ellipse, oval or circle and the distal end 122 can be in the form of an ellipse, oval or circle.

The nasal insert 120 can extend along an axis such that laminar flow can be achieved within and/or between the third 305 and fourth portions 153 of the input/output gas flow passage, and/or within and/or between the second 123 and third 305 portions of the output gas flow passage. Further, the nasal insert 120 can extend along the axis such that laminar flow can be achieved among the third 305 and fourth 153 portions of the input/output gas flow passage and portions of the input gas flow passage upstream and/or downstream of the third 305 and fourth 153 portions, and/or such that laminar flow can be achieved among the second and third portions of the output gas flow passage and portions of the output gas flow passage upstream and/or downstream of the second 123 and third 305 portions.

The seal portion 122 can be disposed adjacent the distal end 130 of the nasal insert 120, and can be adapted to engage the interior portion of the user's nares to thereby retain the ventilation interface 100 therewithin. Although the figures show certain exemplary embodiments of the seal portion 122, it is to be understood that the seal portion 122 can be of any type, so long as the seal portion 122 can engage the interior portion of the nares.

In yet another exemplary embodiment of the invention, the seal portion 122 can include an exterior surface and an interior surface defining a wall portion therebetween, each of the exterior and interior surfaces may have an about C-shaped or arcuate surface and having a circular or oval cross section, such that the seal portion 122 can define the above-identified flow passages. An interior portion of the seal portion 122 can have an interior cross section in the form of an ellipse, or alternatively can have one or both of an interior surface and an exterior surface with an about tear-shaped or optionally a circular cross-section.

In another exemplary embodiment of the invention, the maximum interior cross section and its corresponding circumference may, optionally, be greater than the interior cross section and circumference of the distal end 130 of the nasal insert 120. A maximum exterior cross section and its corresponding circumference of the seal portion 122 may optionally be greater than the exterior cross section and circumference of the distal end 130.

The seal portion 122 and/or the nasal insert 120 can include an elastic material, the resiliency of which may retain the first ventilation interface 100 in the nares. Further, the seal portion 122 and/or the nasal insert 120 can optionally be expanded by the positive pressure of the ventilation gas, thereby aiding in the retention of the first ventilation interface 100 within the nares. Optionally, the nasal insert 120 need not deform when entering the user's nares.

The seal portion 122 can extend along an axis such that laminar flow can be achieved within the fifth portion 152 of the input gas flow passage, and/or within the first portion of the output gas flow passage. Further, the seal portion 122 can extend along the axis such that laminar flow can be achieved between the fifth 152 portion of the input gas flow passage and upstream of the input gas flow passage, and/or such that laminar flow can be achieved between the first 141 portion of the output gas flow passage and downstream of the output gas flow passage. Optionally, the axis is substantially a straight line.

The gas output 150 can be disposed adjacent the cannula body 303 opposite to the nasal insert 120, and can be adapted to channel the gas expired by the user to the exterior of the ventilation interface. Although the figures show certain exemplary embodiments of the gas output 150, it is to be understood that the gas output 150 can be of any type, so long as the gas output 150 can channel the gas expired by the user to an exterior of the ventilation interface 100.

The gas output 150 can define a fifth portion 152 of the output gas flow passage, and more specifically can define the fifth 152 of the output gas flow passage from the cannula body 303 through the gas output. In an exemplary embodiment of the invention, the gas output 150 can include an exterior surface and an interior surface defining a wall portion therebetween, each of the exterior and interior surfaces having a varying cross section including circular shapes, such that the gas output 150 can define the above-identified flow passages. The gas output 150 can have a maximum interior cross sectional area and circumference at a proximal end 141 of the gas output 150 that is adjacent the cannula body 303, thereby defining the fifth 152 portion of the output gas flow passage. The gas output 150 can have a minimal interior cross sectional area and circumference at a distal end 157 of the gas output 150 that is disposed away from the cannula body 303 (i.e., opposite the proximal end 141), thereby defining the fifth 152 portion of the output gas flow passage.

In an exemplary embodiment, laminar flow is achieved among and/or within one or more of the portions (i.e., the first through fifth portions) of the input gas flow passage of the first ventilation interface 100 is achieved among and within all of the portions of the input gas flow passage.

Also as discussed above, the output gas flow passage can channel the expired gas from the nares of the user of the ventilation interface 100, and more specifically can channel the expired gas from of the nares of the user to and through the first portion of the sealing portion 122, to and through the third 305 portion of the distal end 122 of the nasal insert 120, to and through the second 123 portion of the proximal end 121 of the nasal insert 120, to and through the fourth 153 portion of the cannula body 303 of the cannula 300, to and through the fifth 152 portion of the gas output 150, to the exterior of the ventilation interface 100. In an exemplary embodiment of the invention, laminar flow is achieved among and/or within each of the portions (i.e., the first through fifth portions) of the output gas flow passage of the ventilation interface 100, and more optionally is achieved among and within all the portions of the output gas flow passage.

A ventilation interface 100 according to exemplary embodiments of the present invention can avoid disadvantages of the known or conventional ventilation interface requiring a harness.

Referring generally to FIGS. 7–12. In yet another exemplary embodiment of the present invention, the oval feed tubing 500 provides an oval cross-section 505. The distance 503 between the ribs 501 at the bottom surface shorten when bent and the distance between the ribs 504 on the top 502 surface of the tubing wall lengthens in order for the tubing to bend without decreasing the cross-sectional area of the tube. This also gives the oval tubing 500 the ability to drape around the ears of a user. Optionally, circular tubing 600, with a circular cross-sectional are 602, provides ribs 601 which can be bent around the ears.

Figure 9:
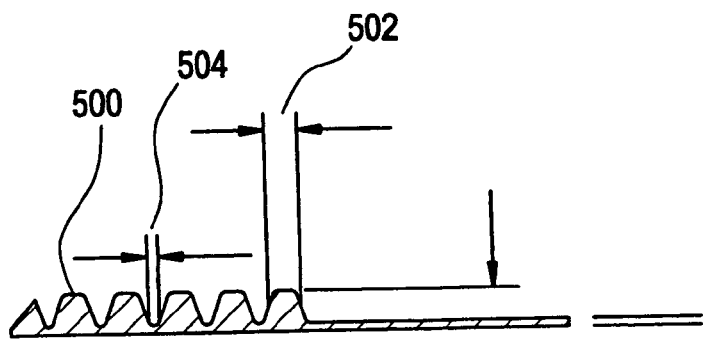
FIG. 9 shows a cross-sectional view of the oval feed tube of FIG. 7.
Figure 9:
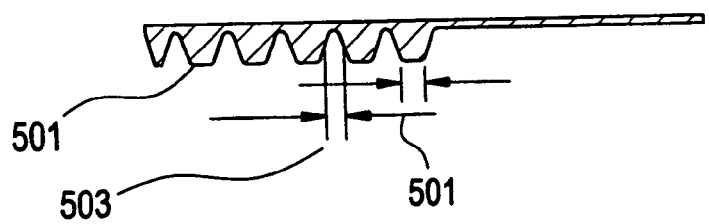
Figure 10:
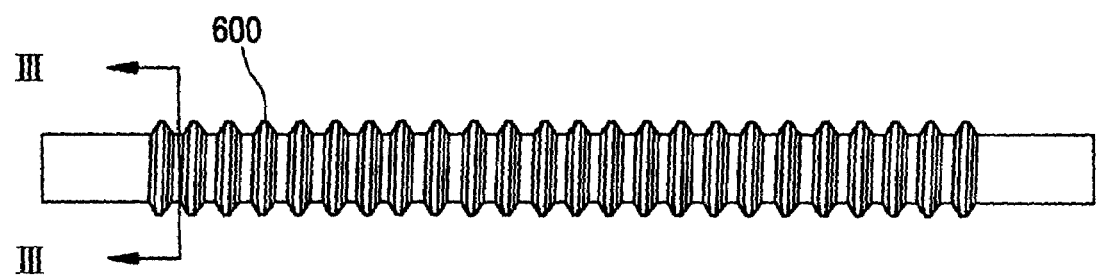
FIG. 10 shows a side view of a round feed tube.
Figure 11:
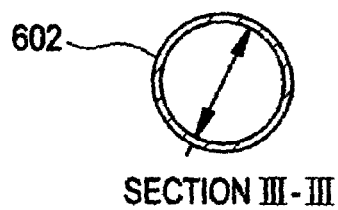
FIG. 11 shows a cross-section of the round feed tube of FIG. 10.
Figure 12:
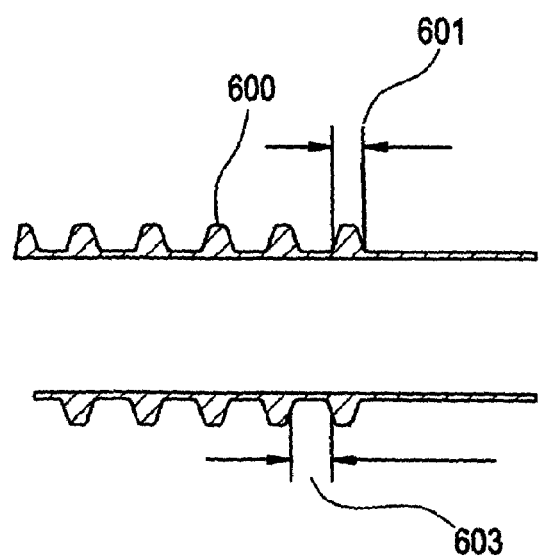
FIG. 12 shows a cross-sectional view of the round feed tube of FIG. 9.
Figure 13:
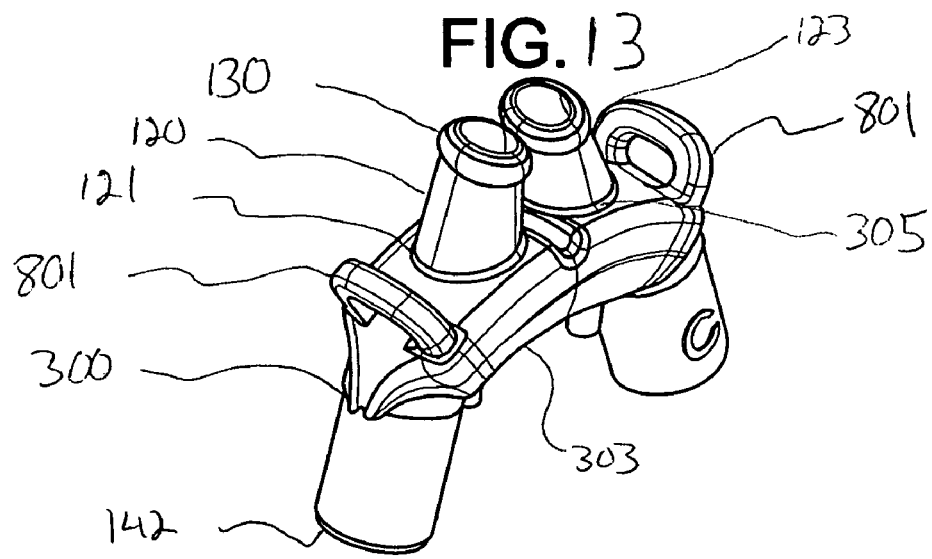
FIG. 13 shows a side elevation view of an exemplary embodiment of a ventilation insert.
Figure 14:
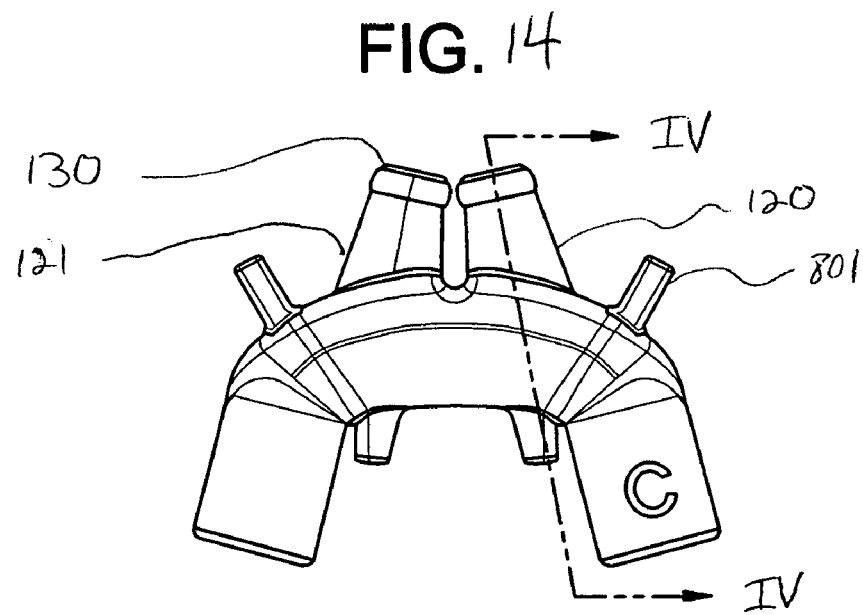
FIG. 14 shows a side view of the ventilation insert of FIG. 13
Figure 15:
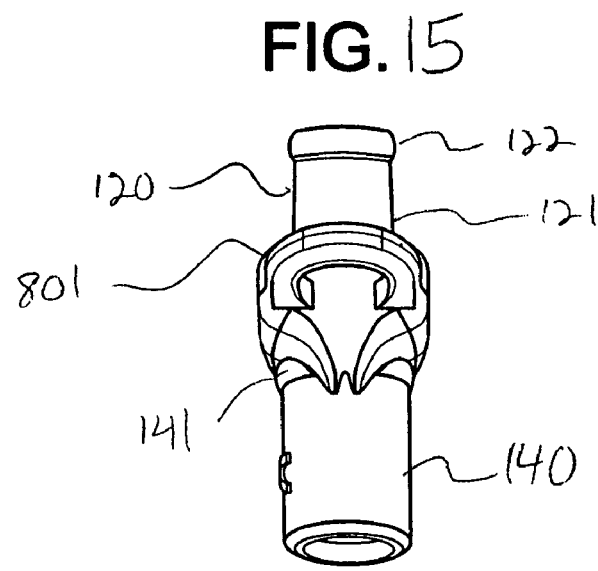
FIG. 15 shows a side view of the ventilation insert of FIG. 13.
Figure 16:
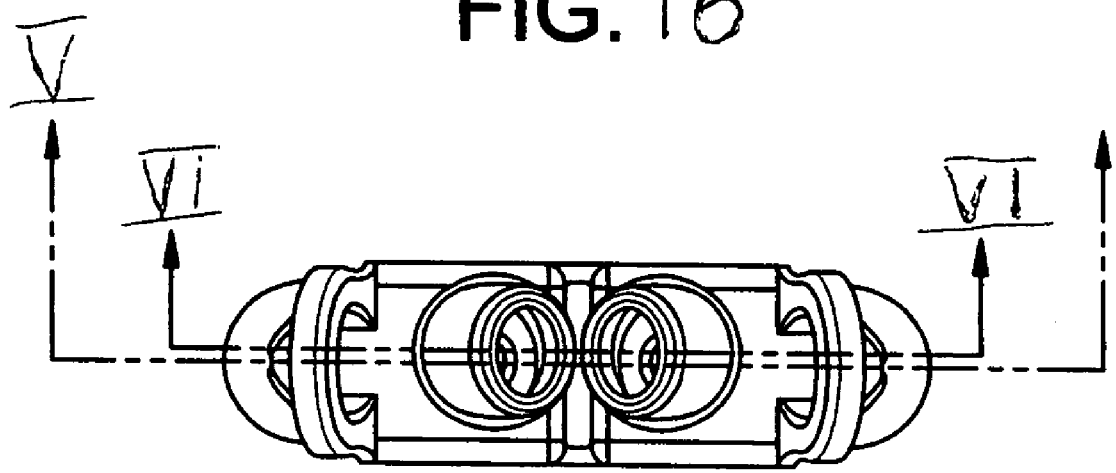
FIG. 16 shows a top view of the ventilation insert of FIG. 13
Figure 17:
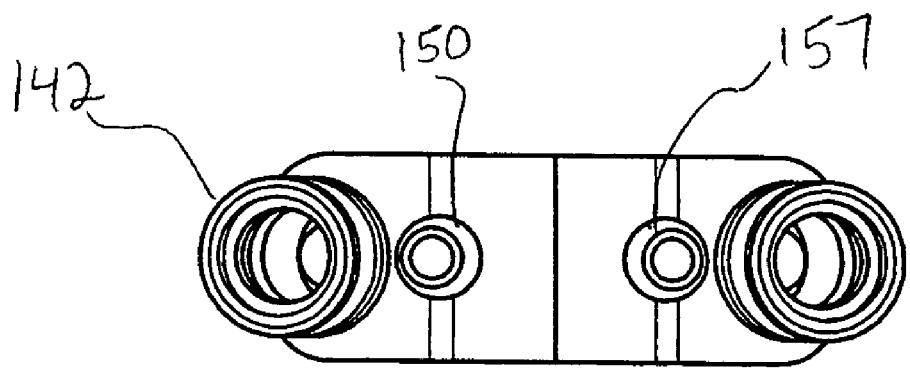
FIG. 17 shows a bottom view of the ventilation insert of FIG. 13
Figure 18:
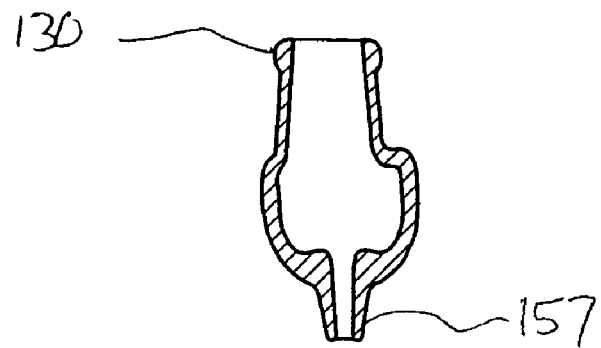
FIG. 18 shows a cross sectional view along the line IV—IV of FIG. 13
Figure 19:
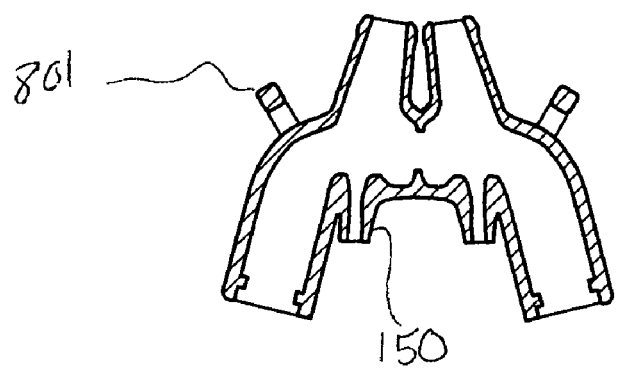
FIG. 19 shows a cross sectional view along the line V—V of FIG. 16.
Figure 20:
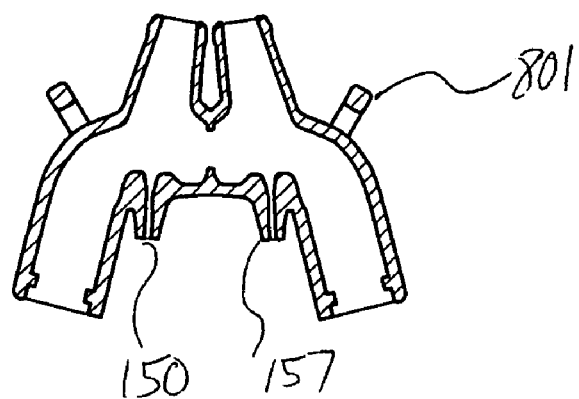
FIG. 20 shows a cross sectional view along the line VI—VI of FIG. 16.

In FIG. 9, the distance between the bottom ribs 503 are spaced when the tubing is straight. When draped in a radius position the distance between the lower ribs 503 is closed and the wall shortens without causing spring-back tension. The points between the top ribs 500 simply separate further at the top when the tube is bent, but not the bottom ribs 503 where the wall thickness is very thin. In between each point of the 500 area there is a slight bend of the thin wall. The accumulation of the sum of each bend gives the radius at the top of the tubing. The accumulation of the compression of the spaces at 503 gives the tubing its radius at the bottom.

Thus, the ventilation interface system according to the exemplary embodiments of the present invention can provide the ventilation gas from the ventilation source to the nares at a lower velocity as compared to the conventional ventilation interface, thereby decreasing an amount of moisture removed from the mucosal walls. Further the ventilation interface system provides better comfort and functionality over the known conventional systems.

Generally referring to FIGS. 13–20 the headgear 700 may be configured to be attached to headgear flange 800, 801. The interaction between the headgear 700 and the headgear flange 800, 801 may hold the nasal inserts in the nares of the user.

Numerous additional modifications and variations of the exemplary embodiments present invention are possible in light of the above teachings. It is therefore to be understood that within the scope of the appended claims, exemplary embodiments of the present invention may be practiced otherwise than as specifically described herein.

What is claimed is:

1. A ventilation interface, comprising:
  a cannula with at least one nasal insert and at least one exhaust port; the cannula forming a first portion of an input gas flow passage to supply the ventilation gas to the user, the first portion of the input gas flow passage defined by a first passage disposed at a first distal end of the cannula where the cannula is connected to a first source of ventilation gas and a second passage disposed at a second distal end of the cannula where the cannula is connected to a second source of ventilation gas;
  the at least one nasal insert forming second and third portions of the input gas flow passage from the cannula to a distal end of the nasal insert that are substantially axially aligned with the first passage disposed at the first distal end of the cannula where the cannula is connected to a first source of ventilation gas and the second passage disposed at the second distal end of the cannula where the cannula is connected to the second source of ventilation gas;
  a seal portion configured to engage at least a portion of the nares, the seal portion being provided on the distal end of the at least one nasal insert; and
  at least one headgear flange disposed the cannula body.

2. The ventilation interface according to claim 1, wherein the first portion of the input gas flow passage defined by a first passage disposed at a first distal end of the cannula where the cannula is connected to a first source of ventilation gas and a second passage disposed at a second distal end of the cannula where the cannula is connected to a second source of ventilation gas, and the second and third portions of the input gas flow passage are disposed at an obtuse angle to one another.

3. The ventilation interface according to claim 1 wherein the headgear flange is configured to receive a headgear strap which holds the nasal insert in place.

4. The ventilation interface according to claim 1, wherein the proximal end of the nasal insert forms a second portion of the input gas flow passage having a substantially oval cross section.

5. The ventilation interface according to claim 4, wherein a distal end of the nasal insert forms a third portion of the input gas flow passage having a substantially oval cross section.

6. The ventilation interface according to claim 5, wherein the third portion of the input gas flow passage has a circumference that is less than a circumference of the second portion of the input gas flow passage.

7. The ventilation interface according to claim 6, wherein the seal portion forms a third portion of the input gas flow passage having a substantially oval cross section.

8. The ventilation interface according to claim 7, wherein the distal end of the nasal insert includes a first exterior portion having a substantially oval cross section.

9. The ventilation interface according to claim 8, wherein the portion of the nasal insert proximal the cannula includes a second exterior portion having a substantially oval cross section.

10. The ventilation interface according to claim 9, wherein the first exterior portion has a circumference that is less than a circumference of the second exterior portion.

11. The ventilation interface according to claim 10, wherein the seal portion includes a third exterior portion having at least one of a substantially oval cross section or a round cross section.

12. The ventilation interface according to claim 11, wherein the third exterior portion has a circumference that is larger than the circumference of the second exterior portion.

13. The ventilation interface according to claim 11, wherein the third exterior portion has a circumference that is substantially equal to the circumference of the second exterior portion.

14. The ventilation interface according to claim 1, further comprising:
  a gas output forming a portion of an output gas flow passage from the nasal insert to an exterior of the ventilation interface to channel a gas expired by the user.

15. The ventilation interface according to claim 14, wherein the second portion of the input gas flow passage formed by the nasal insert is about parallel with the portion of the output gas flow passage.

16. The ventilation interlace according to claim 15, wherein the second portion of the input gas flow passage and the portion of the output gas flow passage are configured to provide laminar flow therebetween.

17. The ventilation interface according to claim 16, wherein a distal end of the gas output forms a first portion of the output gas flow passage having a substantially circular cross section.

18. The ventilation interface according to claim 17, wherein a portion of the gas output proximal the cannula forms a second portion of the output gas flow passage having a substantially circular cross section.

19. The ventilation interface according to claim 18, wherein the first portion of the output gas flow passage has a circumference that is less than a circumference of the second portion of the output gas flow passage.

20. The ventilation interface according to claim 1, wherein at least one of the nasal insert and the seal portion is sufficiently flexible to be expanded by a positive pressure provided by the ventilation gas.

21. The ventilation interface according to claim 1, wherein at least one of the nasal insert and the seal portion forms a seal with the nares of the user by at least one of deformation of at least one of the nasal insert, the nares of the user, the seal portion or a headgear.

22. The ventilation interface according to claim 1, wherein at least one of the nasal insert and the seal portion forms a seal with the nares of the user by friction between the nares of the user and at least one of the nasal insert, the seal portion or a headgear.

23. The ventilation interface according to claim 1, wherein at least one of the nasal inserts and the seal portion form a seal with at least one naris of the user by a resiliency of at least one of said seal portion and said nares of the user and a headgear.

24. A ventilation or CPAP interface system, comprising:
  a cannula, nasal inserts, seal portions and exhaust ports;
  a first feed tube, a second feed tube and a Y-connector;
  a tubing connector;
  head gear;
  the cannula is adapted to be connected to the first feed tube, second feed tube and Y-connector, the cannula forming a first portion of an input gas flow passage, the first portion of the input gas flow passage defined by a first passage that connects to the first feed tube and a second passage that connects to a second feed tube;

the first passage and the second passage of the input gas flow passage being substantially axially aligned with the nasal inserts;

the nasal inserts form a second portion of the input gas flow passage from the cannula to a distal end of the nasal inserts; and a seal portion adapted to engage at least a portion of the nares, the seal portion provided adjacent a distal end of the nasal insert.

25. The ventilation interface according to claim 24, wherein the headgear flange is configured to receive a headgear strap which holds the nasal insert in place.

* * * * *